(12) United States Patent
Wang et al.

(10) Patent No.: US 10,441,180 B2
(45) Date of Patent: Oct. 15, 2019

(54) EPISODICAL AND CONTINUOUS ECG MONITORING

(71) Applicant: Huami Inc., Mountain View, CA (US)

(72) Inventors: Fei Wang, Mountain View, CA (US); Yuanxiang Wang, Mountain View, CA (US)

(73) Assignee: Huami Inc., Mountain View, CA (US)

( * ) Notice: Subject to any disclaimer, the term of this patent is extended or adjusted under 35 U.S.C. 154(b) by 174 days.

(21) Appl. No.: 15/233,103

(22) Filed: Aug. 10, 2016

(65) Prior Publication Data

US 2018/0042502 A1 Feb. 15, 2018

(51) Int. Cl.
*A61B 5/024* (2006.01)
*A61B 5/00* (2006.01)
*A61B 5/0456* (2006.01)
*A61B 5/0476* (2006.01)
*A61B 5/0488* (2006.01)
(Continued)

(52) U.S. Cl.
CPC ........ *A61B 5/02438* (2013.01); *A61B 5/0002* (2013.01); *A61B 5/0008* (2013.01); *A61B 5/0432* (2013.01); *A61B 5/0456* (2013.01); *A61B 5/0476* (2013.01); *A61B 5/0488* (2013.01); *A61B 5/053* (2013.01); *A61B 5/067* (2013.01); *A61B 5/11* (2013.01); *A61B 5/6823* (2013.01); *A61B 5/6824* (2013.01); *A61B 5/0006* (2013.01); *A61B 5/02405* (2013.01); *A61B 5/02416* (2013.01); *A61B 5/04087* (2013.01); *A61B 5/681* (2013.01); *A61B 5/721* (2013.01); *A61B 2560/0209* (2013.01)

(58) Field of Classification Search
CPC ... A61B 5/0002; A61B 5/0006; A61B 5/0008; A61B 5/02405; A61B 5/02416; A61B 5/02438; A61B 5/0456; A61B 5/6823; A61B 5/6824; A61B 5/6831; A61B 5/6898; A61B 5/053; A61B 5/11; A61B 5/1114; A61B 5/1116; A61B 5/112; A61B 5/1121; A61B 5/1122; A61B 5/1123; A61B 5/681; A61B 5/721
USPC ........................................................ 600/509
See application file for complete search history.

(56) References Cited

U.S. PATENT DOCUMENTS 5,226,425 A 7/1993 Righter
5,738,104 A * 4/1998 Lo ...................... A61B 5/02438
600/509
(Continued)

FOREIGN PATENT DOCUMENTS

CN 101547635 A 9/2009
CN 101969840 A 2/2011
(Continued)

*Primary Examiner* — Christopher A Flory
(74) *Attorney, Agent, or Firm* — Young Basile Hanlon & MacFarlane, P.C.

(57) ABSTRACT

Monitoring heart activity using a wearable device, including receiving, from the wearable device, an electrocardiograph (ECG) signal and a motion signal associated with an individual upon contact with the wearable device; in response to receiving the ECG signal and the motion signal associated with the individual, determining, by a computing device, a position of the wearable device in contact with the individual; and determining, by the computing device, a heart activity monitoring mode for operating the wearable device, based on the position of the wearable device in contact with the individual.

19 Claims, 7 Drawing Sheets

(51) Int. Cl.
   *A61B 5/053* (2006.01)
   *A61B 5/11* (2006.01)
   *A61B 5/0432* (2006.01)
   *A61B 5/06* (2006.01)
   *A61B 5/0408* (2006.01)

(56) References Cited

U.S. PATENT DOCUMENTS

| | | | | |
|---|---|---|---|---|
| 7,194,298 B2* | 3/2007 | Massicotte | | A61B 5/0006 600/509 |
| 8,478,403 B2* | 7/2013 | Wenzel | | A61B 5/02125 607/9 |
| 8,688,189 B2* | 4/2014 | Shennib | | A61B 5/0006 600/382 |
| 8,738,118 B2* | 5/2014 | Moon | | A61B 5/0002 600/513 |
| 2006/0264767 A1* | 11/2006 | Shennib | | A61B 5/0006 600/509 |
| 2007/0032733 A1* | 2/2007 | Burton | | A61B 5/02405 600/509 |
| 2007/0279217 A1 | 12/2007 | Venkatraman et al. | | |
| 2008/0021336 A1* | 1/2008 | Dobak, III | | A61B 5/021 600/508 |
| 2009/0270747 A1* | 10/2009 | van Dam | | A61B 5/04525 600/509 |
| 2010/0063365 A1* | 3/2010 | Pisani | | A61B 5/0002 600/301 |
| 2010/0113950 A1 | 5/2010 | Lin et al. | | |
| 2010/0174205 A1* | 7/2010 | Wegerif | | A61B 5/02405 600/515 |
| 2013/0171599 A1* | 7/2013 | Bleich | | A61B 5/0456 434/247 |
| 2013/0178728 A1* | 7/2013 | Vandermeiden | | A61B 5/0245 600/390 |
| 2013/0231947 A1* | 9/2013 | Shusterman | | G06F 19/3418 705/2 |
| 2013/0237772 A1* | 9/2013 | Pisani | | A61B 5/0002 600/301 |
| 2013/0281795 A1 | 10/2013 | Varadan | | |
| 2014/0125618 A1* | 5/2014 | Panther | | A61B 5/6838 345/173 |
| 2014/0135636 A1* | 5/2014 | Kang | | G06K 9/0053 600/509 |
| 2014/0188257 A1* | 7/2014 | Ura | | G09B 19/0038 700/91 |
| 2014/0221849 A1* | 8/2014 | Farringdon | | A61B 5/0428 600/483 |
| 2014/0228665 A1 | 8/2014 | Albert | | |
| 2014/0275852 A1* | 9/2014 | Hong | | A61B 5/02427 600/301 |
| 2014/0288392 A1* | 9/2014 | Hong | | A61B 5/02427 600/301 |
| 2014/0288449 A1* | 9/2014 | Wegerif | | A61B 5/02405 600/509 |
| 2015/0073285 A1 | 3/2015 | Albert et al. | | |
| 2015/0223708 A1* | 8/2015 | Richards | | A61B 5/02427 600/479 |
| 2015/0250396 A1* | 9/2015 | Ahmed | | A61B 5/02405 600/508 |
| 2015/0265214 A1* | 9/2015 | De Kok | | A61B 5/6843 600/301 |
| 2015/0265217 A1* | 9/2015 | Penders | | A61B 5/721 600/301 |
| 2015/0279187 A1* | 10/2015 | Kranz | | G08B 21/0415 340/539.12 |
| 2015/0313476 A1* | 11/2015 | Pisani | | A61B 5/0002 600/301 |
| 2016/0021535 A1* | 1/2016 | Tali | | H04W 68/00 455/411 |
| 2016/0157779 A1* | 6/2016 | Baxi | | A61B 5/6831 600/301 |
| 2016/0174857 A1* | 6/2016 | Eggers | | G06F 19/3418 600/301 |
| 2016/0183869 A1* | 6/2016 | Oh | | A61B 5/7475 600/595 |
| 2016/0192856 A1* | 7/2016 | Lee | | A61B 5/6804 600/384 |
| 2016/0192857 A1* | 7/2016 | Lee | | A61B 5/681 600/382 |
| 2016/0331234 A1* | 11/2016 | Kang | | G06K 9/0053 |
| 2016/0338640 A1* | 11/2016 | Chan | | A61B 5/4884 |
| 2016/0352727 A1* | 12/2016 | Day | | A61B 5/7221 |
| 2017/0049336 A1* | 2/2017 | Hatch | | A61B 5/0456 |
| 2017/0049338 A1* | 2/2017 | Pisani | | A61B 5/0002 |
| 2018/0020980 A1* | 1/2018 | Marcus | | A61B 5/11 |

FOREIGN PATENT DOCUMENTS

| | | |
|---|---|---|
| CN | 104055499 A | 9/2014 |
| CN | 104665823 A | 6/2015 |
| CN | 105615870 A | 6/2016 |

* cited by examiner

EPISODICAL AND CONTINUOUS ECG MONITORING

TECHNICAL FIELD

This disclosure relates in general to heart activity monitoring, and in particular, Electrocardiography (ECG) monitoring.

BACKGROUND

Wearable devices are becoming increasingly commonplace. They may be used in a variety of contexts, such as to monitor the health of a user by measuring vital signals, track a user's exercise and fitness progress, check a user's emails or social media accounts, etc. In certain applications, wearable devices may be configured to measure and monitor signals indicative of electrical activities of the user's heart, such as ECG signals, for detection of certain heart related diseases.

SUMMARY

The present disclosure provides implementations of methods, apparatuses and systems for episodical and continuous ECG monitoring.

According to one aspect of the disclosure, the method includes receiving, from the wearable device, an electrocardiograph (ECG) signal and a motion signal associated with an individual upon contact with the wearable device; in response to receiving the ECG signal and the motion signal associated with the individual, determining, by a computing device, a position of the wearable device in contact with the individual; and determining, by the computing device, a heart activity monitoring mode for operating the wearable device, based on the position of the wearable device in contact with the individual.

In another aspect, the system includes a measurement component, comprising an electrocardiogram (ECG) sensor, comprising a first electrode and a second electrode, wherein first ECG lead of the first electrode configured to generate an ECG signal is formed upon an individual's contact with the first electrode; and a second ECG lead configured to generate the ECG signal is formed upon the individual's contact with the first and second electrodes; and a motion sensor configured to generate a motion signal based on the individual's movement. The system further includes an analysis component comprising a non-transitory memory and a processor configured to execute instructions stored in the non-transitory memory to receive, from the ECG sensor, the ECG signal; receive, from the motion sensor, the motion signal; determine a position of the measurement component in contact with the individual based on the motion signal; and determine a heart activity monitoring mode for operating the measurement component, based on the position of the measurement component in contact with the individual.

In another aspect, an apparatus for monitoring heart activity includes a non-transitory memory and a processor configured to execute instructions stored in the non-transitory memory to receive an electrocardiograph (ECG) signal and a motion signal associated with an individual upon contact with a wearable device; in response to receiving the ECG signal and the motion signal associated with the individual, determine a position of the wearable device in contact with the individual; and determine a heart activity monitoring mode for operating the wearable device, based on the position of the wearable device in contact with the individual, wherein the position of the wearable device in contact with the individual is selected from at least a wrist position and a chest position, and the heart activity monitoring mode for operating the wearable device is selected from at least a first mode indicative of continuous monitoring of ECG signals and a second mode indicative of episodic monitoring of the ECG signals.

These and other aspects of the present disclosure are disclosed in the following detailed description of the embodiments, the appended claims and the accompanying figures.

BRIEF DESCRIPTION OF THE DRAWINGS

The disclosure is best understood from the following detailed description when read in conjunction with the accompanying drawings. It is emphasized that, according to common practice, the various features of the drawings are not to scale. On the contrary, the dimensions of the various features are arbitrarily expanded or reduced for clarity.

The description herein makes reference to the accompanying drawings, where like reference numerals refer to like parts throughout the several views.

DETAILED DESCRIPTION

Figure 1A:
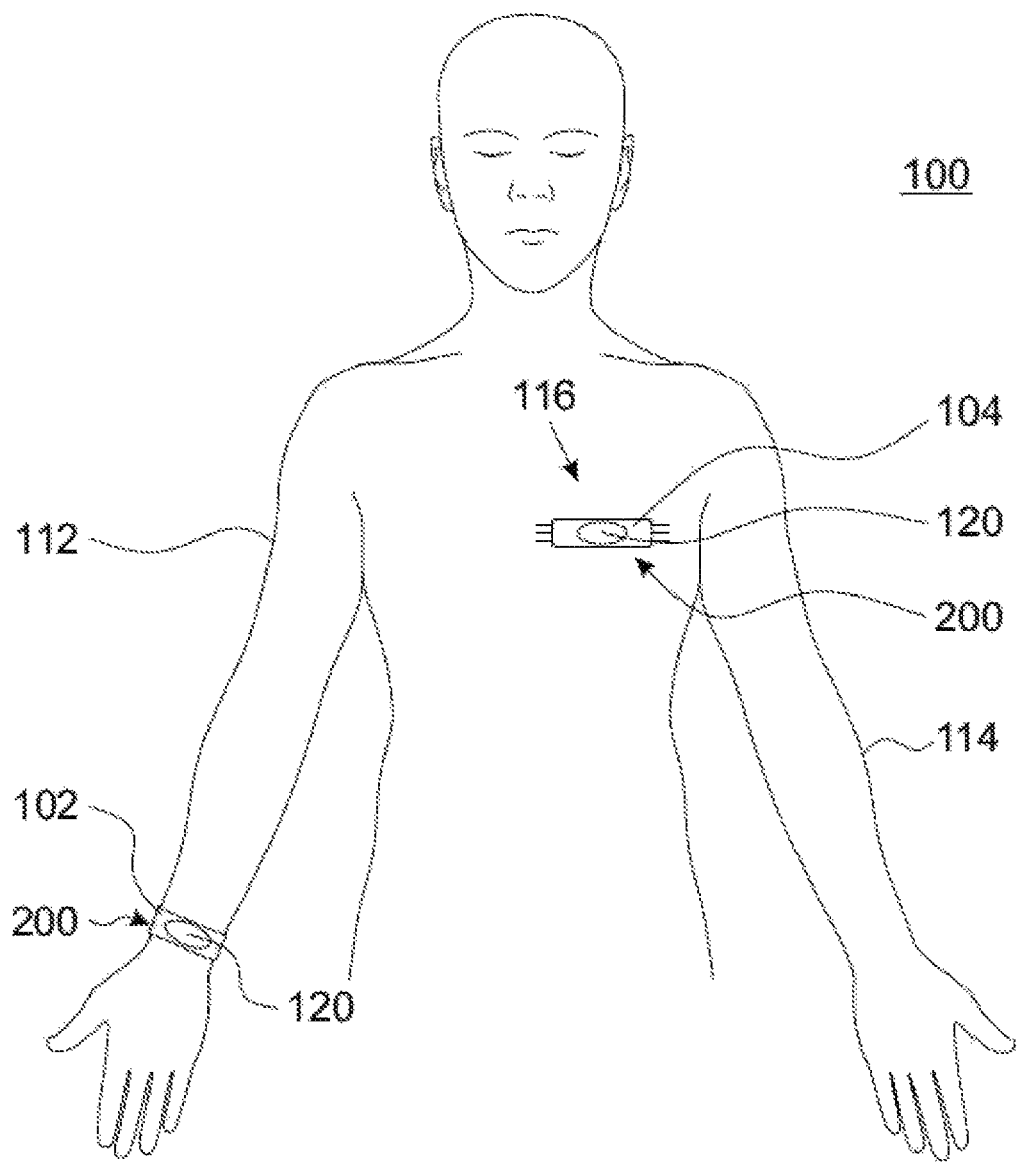
FIG. 1A is a diagram of two example positions of a wearable device worn by an individual according to implementations of this disclosure.

Example implementations of the present disclosure will be described below with reference to the accompanying drawings. The same numbers across the drawings set forth in the following description represent the same or similar elements, unless differently expressed. The implementations set forth in the following description do not represent all implementations or embodiments consistent with the present disclosure; on the contrary, they are only examples of apparatuses and methods in accordance with some aspects of this disclosure as detailed in the claims.

As mobile health care market size keeping growing, devices and systems using wearable technologies to aid fitness or health assessments become more widely used. Among those technologies, mobile or wearable cardiac care devices and systems gain various applications, such as heart disease monitoring and engagement, biometric identification, and fitness tracking.

The wearable device can use various signals measured by various heart rate sensors as input, such as, for example, an electrocardiogram (ECG) signal and/or a photoplethysmogram (PPG) signal. Other sensors can also be used during the operation for additional input, such as a motion sensor. To place the heart rate sensors on a surface of a human body, the wearable devices can use various accessories as secure mechanisms, to which heart rate sensors of the wearable device can be attached.

According to implementations of this disclosure, a wearable device for heart activity monitoring can operate in episodic and continuous operation modes. The position of the wearable device, such as where the wearable device is attached to on the body of an individual can be determined prior to determining an operation mode to be used by the wearable device. The wearable device can work in either an episodic mode or a continuous mode for monitoring heart activities, depending on which body part it attaches to.

The wearable device can operate in at least two operation modes for heart activities monitoring: an episodic mode in which monitoring of heart-related activities is episodic or intermittent; and a continuous mode in which monitoring of heart-related activities is continuous or uninterrupted. Operating in the continuous mode can provide continuous measurement and processing of heart-related data, and further can provide real-time feedback to an individual for a change of cardiac status, such as, for example, recognition of a heart disease or its premonition. Meanwhile, operating in the episodic mode can provide measurements and processing for heart-related data when triggered (e.g., on demand), usually consuming less power and memory compared to the continuous mode, and further can use more sophisticated techniques to process measured data for a wide range of applications such as, for example, disease recognition, biometric identification and determination of fitness or health status (e.g., stress level, fatigue level, or cardiac age).

In some implementations, the wearable device can monitor an ECG signal using one or more electrodes of an ECG sensor. The ECG signal can be either a unipolar an ECG signal or a bipolar ECG signal. For example, in a 12-lead ECG, electrical heart activity of an individual can be recorded from electrodes placed on one or more body surfaces. The 12-lead ECG can provide spatial information about the electrical heart activity, each of the 12 leads representing a particular orientation in space in which the heart's electrical activity is measured. Among the 12 leads, Lead I (right arm to left arm), Lead II (right arm to left leg) and Lead III (left arm to left leg) are bipolar limb leads, and Leads V1, V2, V3, V4, V5 and V6 are unipolar chest leads. To form a bipolar limb lead for measurement, two electrodes need to be in contact with two skin surfaces of two limbs (e.g., right arm and left arm), respectively. To form a unipolar chest lead for measurement, one electrode needs to be in contact with the skin surface of the chest. The wearable device disclosed herein, for example, can have one or more electrodes, in which a bipolar limb lead can be formed when a different electrode of at least two electrodes get in contact with a surface of a different limb, or a unipolar chest lead can be formed when one of the electrodes get in contact with a surface on the chest. The term "contact" herein can refer to an electrode having a direct contact with bare skin, or the electrode having an indirect contact with bare skin with conductive material in between (e.g., a conductive patch or a conductive suit).

Figure 1B:
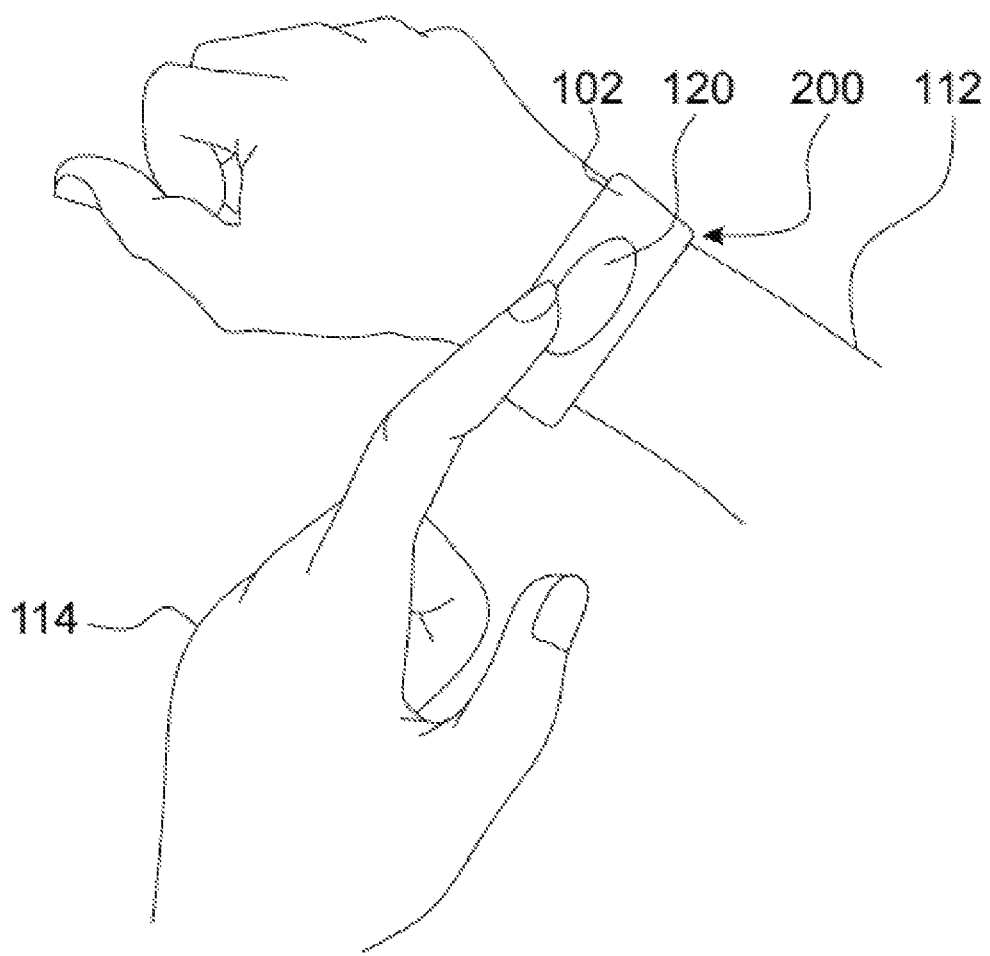
FIG. 1B is a diagram of an example configuration when an electrocardiogram (ECG) signal can be received by the wearable device of FIG. 1A.

FIGS. 1A and 1B are diagrams showing some example positions of a wearable device worn by an individual according to implementations of this disclosure. As used throughout this disclosure, a wearable device can be implemented as any suitable wearable device, such as a device core, brace, wristband, limb band, leg band, ring, headband, or the like. In some implementations, the wearable device can include a portable component configured to travel with but not be worn by an individual, such as a key fob.

FIG. 1A is a diagram of two example positions of a wearable device 200 worn by an individual according to implementations of this disclosure. Wearable device 200 can include, for example, a device core 120 and one or more accessory components as housing, such as a wrist band 102 or a chest patch 104, as shown in FIG. 1A. Wearable device 200 can include an electrocardiogram (ECG) component (e.g., an ECG sensor) comprising a first electrode and a second electrode (not shown) configured to measure various aspects of the individual's heart function and related biometrics. The ECG component, e.g., ECG sensor, can be included in or otherwise become part of device core 120. The ECG component can also be implemented as a separate component attachable to the main body of device 200.

In one example, the accessory component can include a wrist band 102, and device core 120 can be removably attached to the wrist band 102. In this setting (also referred to as the "wrist position"), device 200 can be attached to a wrist of the individual (on either limb, e.g., right limb 112 in FIG. 1A). The first electrode of the ECG sensor is coupled to an interior surface of device 200 facing skin of the individual that is wearing device 200, in this case the individual's wrist. The second electrode is coupled to an exterior surface of device 200 and is not in direct contact with the individual that is wearing device 200. The first electrode may or may not be in contact with the wrist at all times when device 200 is worn. The first electrode and the second electrode are configured to identify electrical heart activity and transmitting the measurement data for subsequent processing. That is, upon the individual contacting second electrode, for example with a finger, the first electrode, if not already in contact with the individual's skin, contacts the skin to form a single lead ECG sensor, which permits device 200 to measure the individual's heart activity. A bipolar ECG signal (e.g., Lead 1) can be received by device 200, for example.

In another example, the accessory component can include a chest patch 104, which can be attached to the chest 116 of the individual, and device core 120 can be removably attached to chest patch 104. Chest patch 104 can be, for example, an adhesive patch, a sticker, or the like. When attached to the chest of the individual, the first electrode of the ECG sensor on the interior surface facing the skin of the individual can be in contact with the skin of chest 116, which can form the lead to generate the electronic signals for heart activity measurements. A unipolar ECG signal (e.g., Lead V1, V2, V3, V4, V5 or V6) can be received by device 200, for example.

FIG. 1B shows an example configuration when a bipolar ECG signal (e.g., Lead I) can be received by wearable device 200. In this example, device 200 is worn on the wrist of the right limb 112 of the individual. The first electrode on the interior surface of device 200 may or may not already be in contact with the individual's skin. When the individual contacts the second electrode on the exterior surface of device 200 using, for example, a fingertip of the left limb 114, the first electrode, if not already in contact with the individual's skin, contacts the skin to form a bipolar ECG lead, which permits measurement component 200 to receive a bipolar ECG signal (e.g., Lead I).

Depending on where (e.g., which part of the individual's body) device 200 is being attached to the body of the individual, the wearable device can operate in different modes, as will be described in detail below. In the examples, device 200 operate in a continuous mode for measuring unipolar heart activity signals when attached to the chest ("chest position"), and operate in an episodic mode for measuring bipolar heart activity signals when attached to the wrist ("wrist position"). Variations, modifications, and other arrangements are possible and not limited to the examples herein. For example, each of the operating modes (e.g., episodic or continuous) can be used to measure either unipolar or bipolar heart rate signals, in other configurations.

Figure 2:
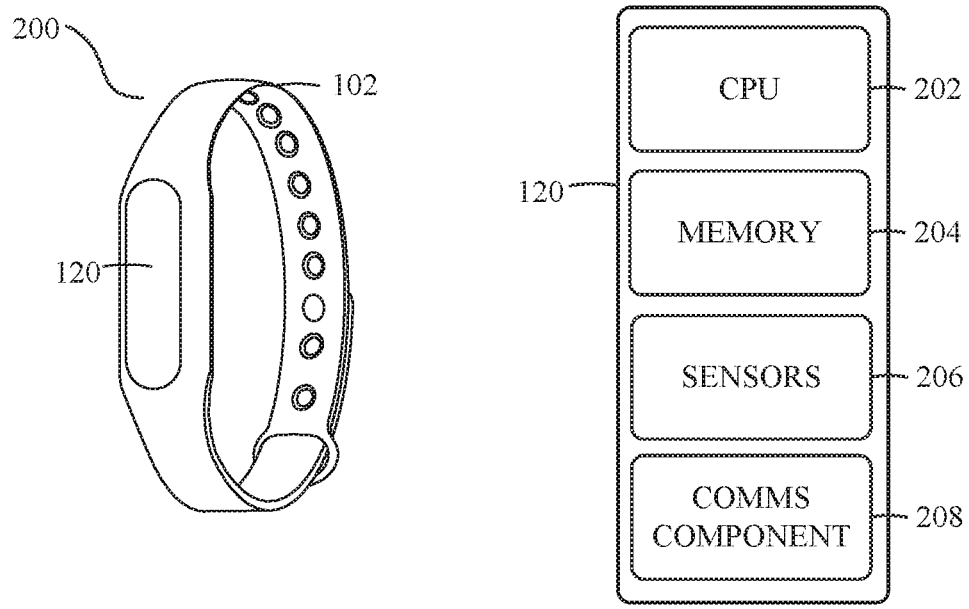
FIG. 2 is a diagram of an implementation of a wearable device usable within implementations of the disclosure.

FIG. 2 is a diagram of an implementation of a wearable device 200 usable within implementations of the disclosure. Wearable device 200 can be the wearable device discussed above with respect to FIGS. 1A and 1B. For example, wearable device 200 can include a device core 120 and one or more accessory components as housing, such as a band 102 or a chest patch (not shown).

In an implementation, device core 120 comprises CPU 202, memory 204, sensors 206, and communications component 208. One example of CPU 202 is a conventional central processing unit. CPU 202 may include single or multiple processors each having single or multiple processing cores. Alternatively, CPU 202 may include another type of device, or multiple devices, capable of manipulating or processing information now-existing or hereafter developed. Although implementations of wearable device 200 can be practiced with a single CPU as shown, advantages in speed and efficiency may be achieved using more than one CPU.

Memory 204 can comprise random access memory device (RAM) or any other suitable type of storage device. Memory 204 may include executable instructions and data for immediate access by CPU 202, such as data generated and/or processed in connection with sensors 206. Memory 204 may include one or more DRAM modules such as DDR SDRAM. Alternatively, memory 204 may include another type of device, or multiple devices, capable of storing data for processing by CPU 202 now-existing or hereafter developed. CPU 202 may access and manipulate data in memory 204 via a bus.

Sensors 206 can be one or more sensors disposed within or otherwise coupled to wearable device 200, for example, for identifying, detecting, determining, or otherwise generating signal data indicative of measurements associated with device 200 and/or an individual wearing device 200. In an implementation, sensors 206 can comprise one or more electromyography sensors, accelerometers, cameras, light emitters, touch sensors, or the like. The accelerometers can be three-axis, six-axis, nine-axis or any other suitable accelerometers. The cameras can be RGB cameras, infrared cameras, monochromatic infrared cameras, or any other suitable cameras. The light emitters can be infrared light emitting diodes (LED), infrared lasers, or any other suitable lights. Sensors 206 can comprise one or more sensors that can generate heart activity signals such as an electroencephalogram (EEG) sensor, a PPG sensor, an electromyogram (EMG) sensor, or the like. For example, the ECG sensor can comprise a first electrode arranged in an interior surface of device core 120, which can be in contact with the skin of an individual when worn, and a second electrode arranged in an exterior surface of device core 120. Sensors that can be included in the wearable device 200 can also include sensors capable of generating biometric signals, such as ECG signals, through non-invasive techniques such as without contacting the skin of the individual.

Sensors 206 can also comprise one or more bioimpedance sensors, microphones, temperature sensors, touch screens, finger readers, iris scanners, a combination of the above, or the like. Implementations of sensors 206 can include a single sensor, one of each of the foregoing sensors, or any combination of the foregoing sensors. In an implementation, the signal data can be identified, detected, determined, or otherwise generated based on any single sensor or combination of sensors included in wearable device 200.

Communications component 208 can be a hardware or software component configured to communicate data (e.g., measurements, etc.) from sensors 206 to one or more external devices, such as another wearable device or a computing device, for example. In an implementation, communications component 208 comprises an active communication interface, for example, a modem, transceiver, transmitter-receiver, or the like. In an implementation, communications component 208 comprises a passive communication interface, for example, a quick response (QR) code, Bluetooth identifier, radio-frequency identification (RFID) tag, a near-field communication (NFC) tag, or the like. Communication component 208 can operate over wired or wireless communication connections, such as, for example, a wireless network connection, a Bluetooth connection, an infrared connection, an NFC connection, a cellular network connection, a radio frequency connection, or any combination thereof. In some implementations, communication component 208 can use sound signals as input and output, such as, for example, an ultrasonic signal or a sound signal via an audio jack. Implementations of communications component 208 can include a single component, one of each of the foregoing types of components, or any combination of the foregoing components.

Wearable device 200 can also include other components not shown in FIG. 2. For example, wearable device 200 can include one or more input/output devices, such as a display. In an implementation, the display can be coupled to CPU 202 via a bus. In an implementation, other output devices may be included in addition to or as an alternative to the display. When the output device is or includes a display, the display may be implemented in various ways, including by a LCD, CRT, LED, OLED, etc. In an implementation, the display can be a touch screen display configured to receive touch-based input, for example, in manipulating data output to the display.

Figure 3:
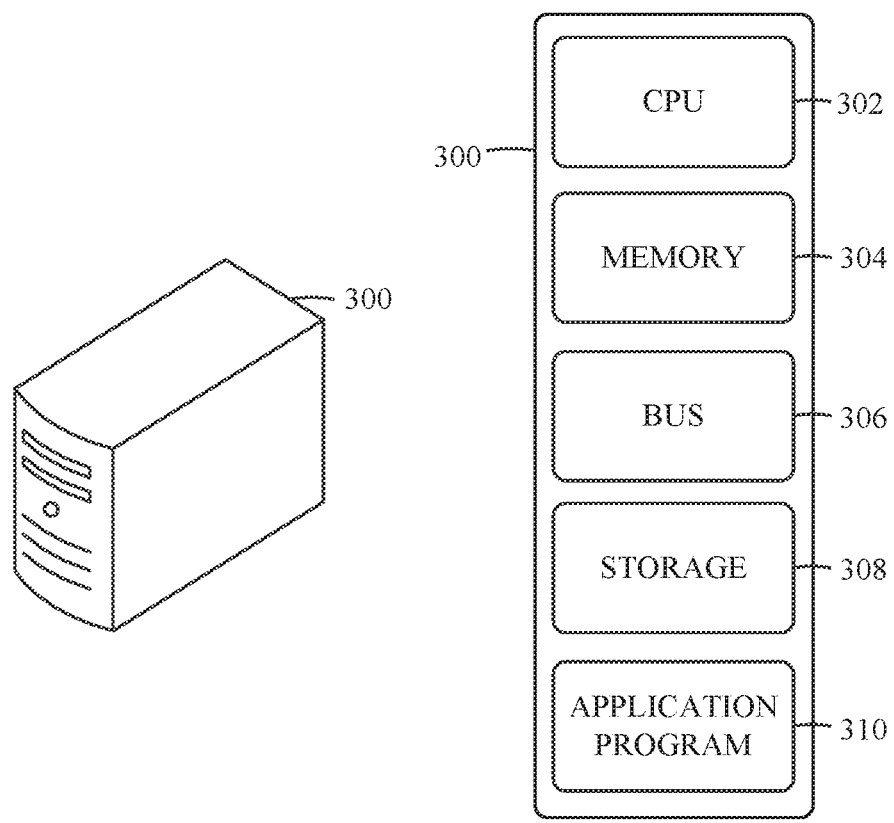
FIG. 3 is diagram of an example computing device and an example hardware configuration of the computing device according to implementations of this disclosure.

FIG. 3 shows a computing device 300 as an example and a block diagram of a hardware configuration of computing device 300 according to implementations of this disclosure. Computing device 300 can be a part of the system for heart activity monitoring disclosed herein. In some implementations, computing device 300 and wearable device 200 (or any device having measurement capabilities) can be the same device. Computing device 300 can be shown as an example type of computer in FIG. 3, but it is not limited to any specific type or any specific quantity in the system disclosed herein. Computing device 300 can be implemented by any configuration of one or more computers, such as a microcomputer, a mainframe computer, a super computer, a general-purpose computer, a special-purpose/dedicated computer, an integrated computer, a database computer, a remote server computer, a personal computer, a laptop computer, a tablet computer, a cell phone, a personal data assistant (PDA), a wearable computing device, e.g., a smart watch, or a computing service provided by a computing service provider, e.g., a website, or a cloud service provider. In some implementations, computing device 300 can be a smart phone device that can be used to display and analyze ECG signals. In some implementations, certain operations described herein can be performed by a computer (e.g., a server computer) in the form of multiple groups of computers that are at different geographic locations and can or cannot communicate with one another by way of, such as, a network. While certain operations can be shared by multiple computers, in some implementations, different computers can be assigned with different operations.

Hardware configuration 300 can include at least one processor such as CPU 302. CPU 302 as well as CPU 202 can be any type of device, or multiple devices, capable of manipulating or processing information. Although the examples herein can be practiced with a single processor as shown, advantages in speed and efficiency can be achieved using more than one processor. CPU 302 can be distributed across multiple machines or devices (each machine or device having one or more of processors) that can be coupled directly or across a local area or other network. Although the examples herein can be practiced with a single processor as shown, advantages in speed and efficiency can be achieved using more than one processor.

Memory 304 as well as memory 204 can be, for example, a random access memory device (RAM), a read-only memory device (ROM), an optical disc, a magnetic disc, or any other suitable type of storage device, and can store code and data that can be accessed by CPU 302 using a bus 306. Although a single bus 306 is depicted, multiple buses can be utilized. Memory 304 can be distributed across multiple machines or devices such as network-based memory or memory in multiple machines performing operations that can be described herein as being performed using a single computing device for ease of explanation. The code can include an operating system and one or more application program 310 processing and/or outputting the data. As will be discussed in detail below, application program 310 can include software components in the form of computer executable program instructions that cause CPU 302 to perform some or all of the operations and methods described herein. In some implementations, hardware configuration 300 is used to implement computing device 300 or at least an analysis component of computing device 300, in which application program 310 stored by memory 304 can implement some or all of the processes as described in more detail below.

Hardware configuration 300 can optionally include a storage device 308 in the form of any suitable non-transitory computer readable medium, such as a hard disc drive, a memory device, a flash drive or an optical drive. Storage device 308, when present, can provide additional memory when high processing requirements exist. Storage device 308 can also store any form of data, relating or not relating to cardiac information. Further, storage device can be a component of hardware configuration 300 or can be a shared device that is accessed via a network.

Hardware configuration 300 can include more devices or components. For example, computing device can further include one or more input devices, output devices, communication devices, or any other device that can be used to transmit, store, process, and present data.

Although FIG. 3 depicts one hardware configuration 300 that can implement computing device 300, other configurations can be utilized. The hardware configuration of a computing system as depicted in an example in FIG. 3 thus can be implemented in a wide variety of configurations.

Figure 4:
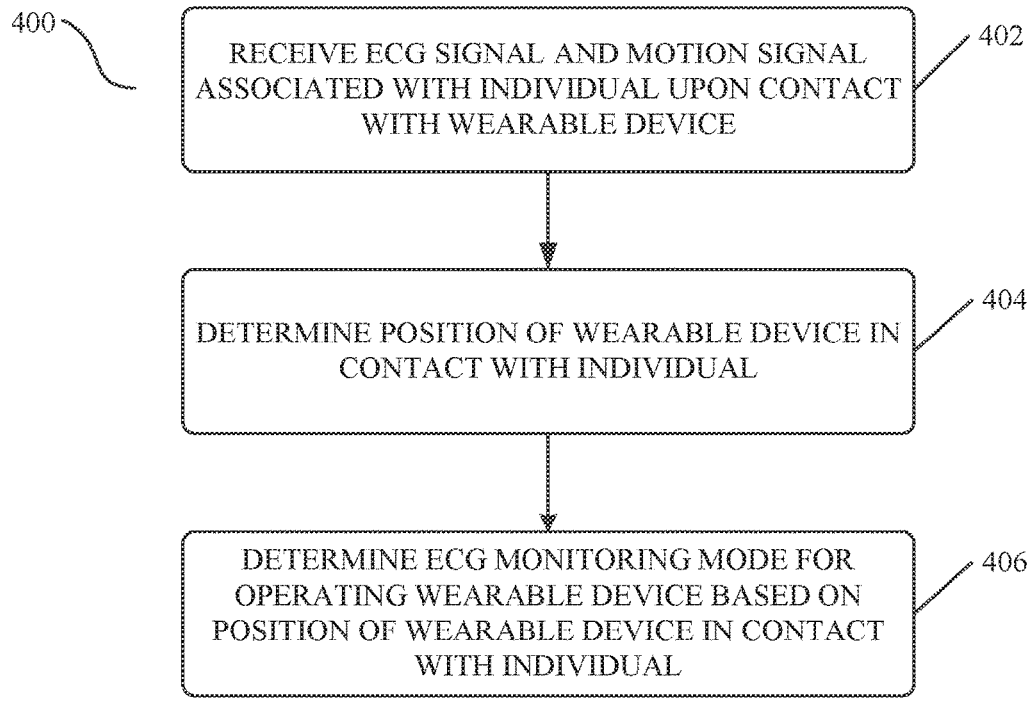
FIG. 4 is a diagram of an example process of heart activity monitoring using a wearable device according to implementations of this disclosure.

FIG. 4 is a block diagram of an example process of monitoring heart activity using a wearable device according to implementations of this disclosure. Implementations of block diagram 400 can be performed entirely on a wearable device (e.g., wearable device 200) on which the sensor data is collected or generated, or on another wearable device and/or a computing device (e.g., computing device 300) in communication with one or more wearable devices. For example, the sensor data processing aspects of block diagram 400 can be performed by instructions executable on the computing device. In some implementations, portions of block diagram 400 can be performed by instructions executable on the computing device and/or one or more other devices, such as a wearable device. In some implementations, computing device 300 can be a cell phone or a wearable device such as a smart watch, which can receive and display signals. In some implementations, computing device 300 can be a cloud server. The heart activity being monitored can include, for example, prediction data or events associated with certain heart diseases ("disease prediction"). In addition, wearable device 200 can be used for prediction data or events associated with fitness activities ("fitness prediction"), or biometric identification. The fitness activities can include, for example, emotion, stress, or heart age prediction.

At operation 402, an electrocardiograph (ECG) signal and a motion signal associated with an individual are received. The ECG signal and the motion signal can be generated by wearable device 200 upon detecting a contact by the individual with wearable device 200. The ECG signal and the motion signal can be received by wearable device 200 and/or computing device 300.

Sensor signals, such as the ECG signal and the motion signal, can be generated and outputted by, for example, one or more sensors in wearable device 200. Examples of generating the ECG signal have been described in FIGS. 1A, 1B, such as, for example, when at least one of the electrodes of an ECG sensor gets in contact with the skin of the individual. Wearable device 200 can be in contact with the individual by one or more electrodes of the ECG sensor(s) included in the wearable device. For example, the individual can get in contact with the wearable device by one of tapping, pressing, holding, wearing or otherwise touching one or more electrodes of wearable device 200. For example in FIG. 1A, once wearable device 200 is worn on the individual's chest or wrist, the individual is in contact with wearable device 200, upon which the ECG signal and the motion signal can be generated.

The motion signal can be generated by a motion sensor in wearable device 200, which can be used to determine linear or angular motion characteristics of wearable device 200, such as, for example, velocity, acceleration, speed, direction, or inertia. In some implementations, the motion sensor can be an accelerometer, a gyroscope, a magnetometer, an Inertial Measurement Unit (IMU), or any combination of any sensor for detecting motion characteristics of the wearable device. When the individual is wearing the wearable device 200 on a body part (e.g., wrist or chest), the motion signal can be used to indicate the motion characteristics of that body part of the individual.

In some implementations, the ECG signal and the motion signal can be received by the wearable device. In some other implementations, the ECG signal and the motion signal can be received by the wearable device and transmitted to another computing device, such as computing device 300. The "receiving" used herein can refer to receiving, inputting, acquiring, retrieving, obtaining, reading, accessing, determining, or in any manner inputting data. The ECG signal and the motion signal can be received concurrently, or at different times. As used herein, information, signals, or data are received by transmission or accessing the information, signals, or data in any form, such as receiving by transmission over a network, receiving by accessing from a storage device, or receiving by individual operation of an input device.

At operation 404, in response to receiving the ECG signal and the motion signal associated with the individual, a position of the wearable device in contact with the individual is determined. The position of the wearable device in contact with the individual can be a position of the individual body where the wearable device is worn, such as the positions shown in FIGS. 1A-1B. The position can be on, for example, a limb end (e.g., a wrist, an ankle), an arm, a leg, chest, torso, etc. The position of the wearable device in contact with the individual can be determined based on the received signals, for example, at least one of the motion signal and the ECG signal received at operation 402. In some implementations, the position can be determined based on the motion signal without using the ECG signal. In some other implementations, the position can be determined based on both the motion signal and the ECG signal. For example, to determine the position of wearable device 200, the motion signal data (e.g., accelerator signal data) can be input to rule-based or statistical models, which can be generated by offline training based on labeled data (e.g., data associated with known body positions). By analyzing the motion characteristics of wearable device 200 upon receiving the ECG signal, the position of wearable device 200 can be determined automatically, which can be used to select a heart activity monitoring mode for operating wearable device 200. Details of determining the position of the wearable device are set forth in the following description of FIG. 5.

At operation 406, a heart activity monitoring mode for operating the wearable device is determined based on the position of the wearable device in contact with the individual. The heart activity being monitored can include, for example, prediction events associated with certain heart diseases ("disease prediction"). For example, the heart activity monitoring mode can be a heart disease monitoring mode that is capable of detecting cardiac disease in real time. Different heart activity monitoring modes can be used to monitor heart activities episodically or continuously. The modes can be triggered or activated based on the position of wearable device 200 in contact with the individual. In each heart activity monitoring mode (e.g., episodic mode and continuous mode), a different operations can be performed accordingly by wearable device 200, examples of which are shown and described in FIGS. 5-7.

Figure 5:
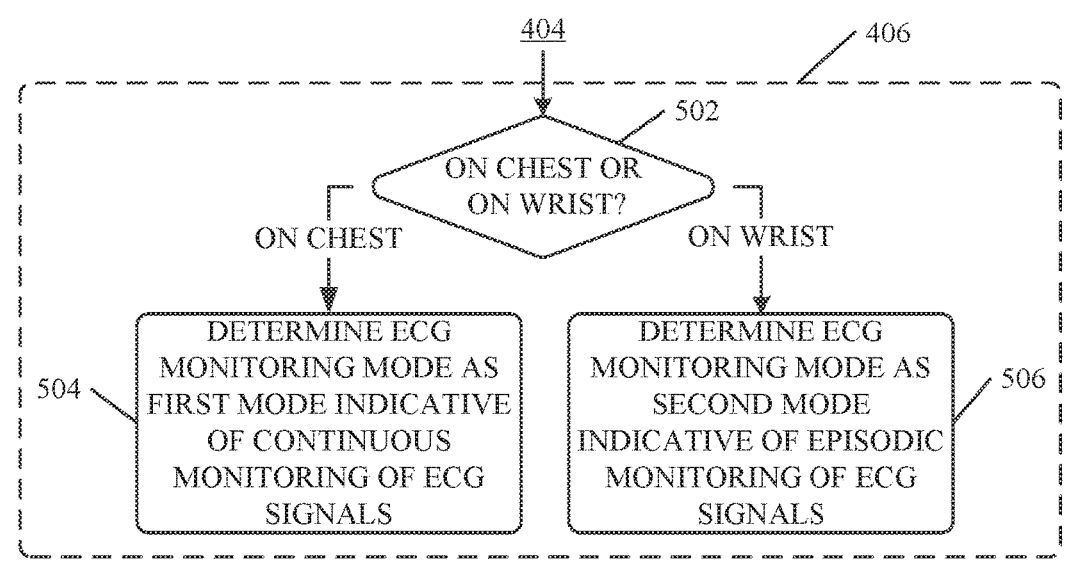
FIG. 5 is an example process of determining a heart activity monitoring mode according to implementations of this disclosure.

FIG. 5 is an example process 500 of determining a heart activity monitoring mode according to implementations of this disclosure. Process 500 can be implemented by or incorporated into operation 406 of FIG. 4, for example.

At operation 502, it can be determined whether the position of the wearable device in contact with the individual is a chest position or a wrist position. The position of the wearable device in contact with the individual can be determined at, for example, operation 404, based on the motion signal and/or ECG signal. The motion characteristics extracted from the measured motion signal can have different patterns for one or more body parts in motion (e.g., the wrist position or the chest position), which can be compared with predetermined characteristics associated with the one or more body parts. If a match between the extracted motion characteristics and a predetermined characteristics associated with a specific body part is found as a result of the comparison, the position of the wearable device can be determined as that body part. The predetermined characteristics can be, for example, profile data determined from a training process, which can be based on labelled data associated with known positions.

At operation 504, when the wearable device is determined to be on the chest, the heart activity monitoring mode for operating the wearable device is determined as a mode indicative of continuous monitoring of ECG signals received by the wearable device. This mode is also referred to as "continuous mode" or "first mode". When operating in the continuous mode, the wearable device can monitor the ECG signals continuously for the individual ("continuous monitoring"). For example, monitoring of the ECG signals can be continuous until wearable device 200 exits the first mode, such as, for example, the individual takes the wearable device 200 off the chest position. An example process of continuous monitoring in the first mode is described below in FIG. 6.

At operation 506, when the wearable device is determined to be on the wrist, the heart activity monitoring mode for operating the wearable device is determined as a mode indicative of episodic monitoring of ECG signals received by the wearable device. This mode is also referred to as "episodical mode" or "second mode". When operating in the episodical mode, the wearable device can monitor the ECG signals episodically for the individual ("episodical monitoring"). The monitoring of the ECG signals in the epsodical mode can be triggered by, for example, a further action of the individual. For example, when wearable device 200 is worn on and therefore in contact with the wrist of the individual by a first electrode on a first surface (e.g., an interior surface of the wrist band), a triggering action can be when the individual touches a second electrode on a second surface (e.g., an exterior surface) with another hand (e.g., a fingertip of the other hand). The episodical mode can be triggered and performed for a certain period of time, such as, for example, for several seconds or minutes. An example process of episodical monitoring in the second mode is described below in FIG. 7.

In some implementations, the position of the wearable device can be determined based on the motion signal without using the ECG signal. In other implementations, the position of the wearable device can be determined based on both the motion signal and the ECG signal. For example, when the ECG signal is received from two electrodes, the ECG signal can be determined as a bipolar limb lead (e.g., Lead I, II, or III). Based on the motion characteristics determined from the motion signal, the position of the wearable device being worn can be determined as on a limb position (e.g., a wrist). In another example, when the ECG signal is received from only one electrode, the ECG signal can be determined as a unipolar lead (e.g., Lead V1, V2, V3, V4, V5, or V6), which is commonly used as a chest lead. Based on the results of the motion characteristics comparison and the lead type, the position of the wearable device can be determined, such as on chest or another position. Other than the examples disclosed herein, the methods and processes to determine the position of the wearable device or the measurement component can use any combination of any sensor data as input. In addition, the "wrist position" and the "chest position" are just two examples of body positions. Other positions that can be used include, for example, a limb position (e.g., on arm, leg, knee, or ankle), a shoulder position, a torso position (e.g., on chest or abdomen), or any other body position of an individual that can be used to measure an ECG signal. Details of operating in different heart activity monitoring modes (e.g., continuous mode or episodic mode) will be described below in FIGS. 6 and 7.

Figure 6:
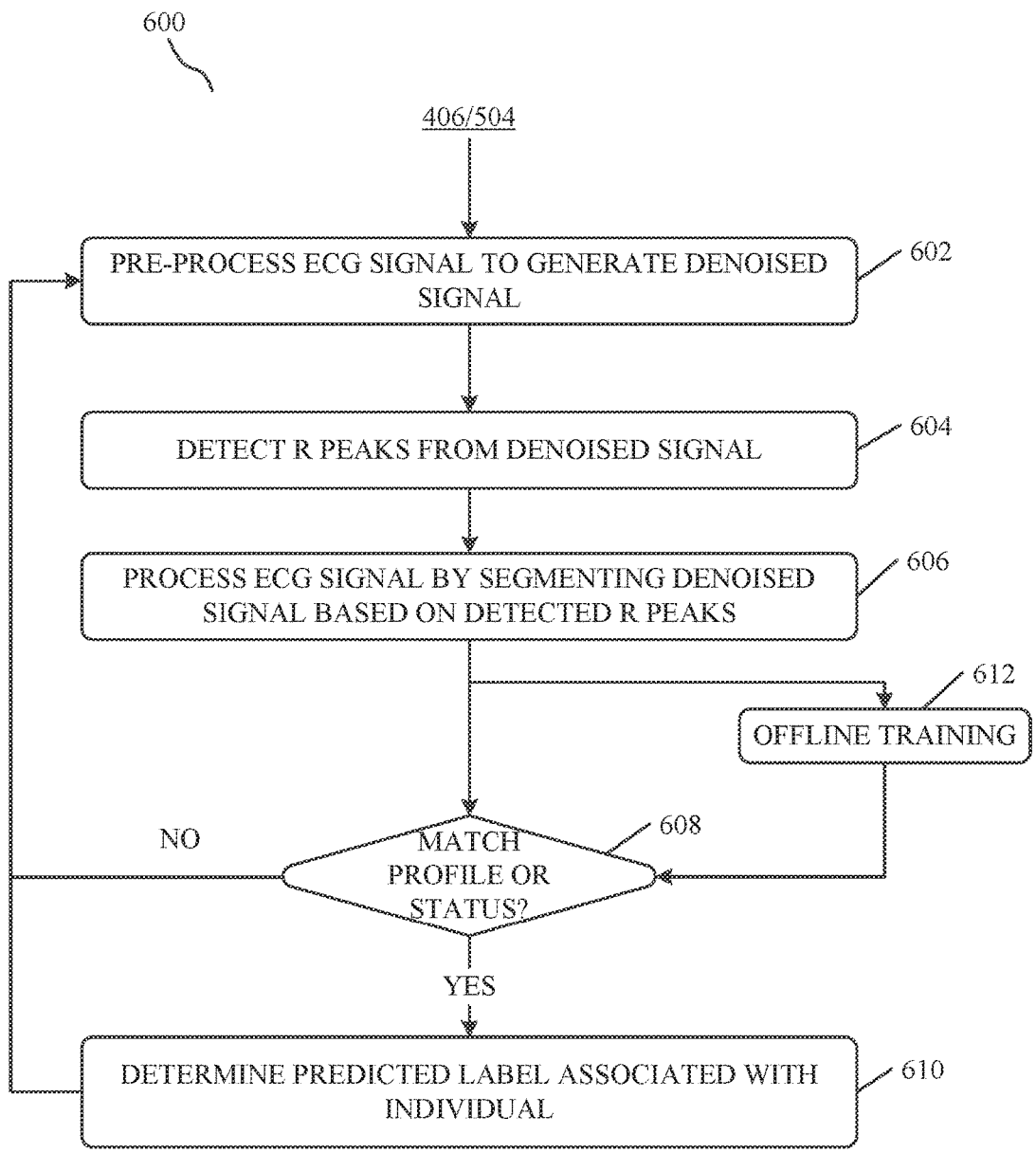
FIG. 6 is a flow diagram showing an example process for continuous ECG monitoring according to implementations of this disclosure.

FIG. 6 is a flow diagram showing an example process 600 for continuous monitoring of heart activity ("continuous mode"). Process 600 can be carried out following process 400 or 500, for example, upon determining that continuous mode is to be used for monitoring the ECG signals at operation 406 or 504. For example, process 600 can be triggered when it is determined that continuous mode is to be used for operating the wearable device at operation 504. Process 600 can also be activated by the individual by manually setting the operating mode as the continuous mode by software or hardware, such as by application program 310. The continuous mode can monitor heart activity of the individual in real-time and further provide feedback data to the individual. The feedback data can include data indicative of, for example, a heart disease or a health status.

At operation 602, the received ECG signals are pre-processed to generate a denoised signal. The term "noise" of a signal can herein refer to any artifact or background that obscures or reduces the clarity of the signal (e.g., disturbance, distortion, or deviation). Sources of noise of the ECG signal can include, for example, EMG background, baseline wandering, powerline interference, and motion artifacts. The pre-processing can perform operations to reduce or remove the noise from the ECG signal.

At operation 604, R peaks are detected from the denoised ECG signal. The ECG signal can include PQRST cycles. A PQRST cycle of an ECG signal is defined as a portion of the ECG signal that represents one complete heartbeat, which consists of a P wave, a QRS complex and a T wave connected in temporal order. The peak of a QRS complex is defined as an R peak, and a time interval between two adjacent R peaks ("RR interval") represents the length of a heartbeat.

At operation 606, the ECG signal is processed by segmenting the denoised signal based on the detected R peaks. For example, after detecting R peaks, ECG periodic fragments (e.g., QRS complexes) can be extracted from the denoised signal by directly taking signal data around the R peaks, or by any other technique that can be used to extract ECG periodic segments.

At operation 608, it is determined whether the processed ECG signal matches a predefined profile. The profile can include template data that can be extracted from a training process such as an offline training operation 612. The profile can be associated with, for example, a known disease ("disease profile") or a known individual ("individual profile"). For example, a disease profile can be associated with, for example, a premature ventricular contraction (PVC) event, a premature atrial contraction (PAC) event, a ventricular tachycardia event, an atrial fibrillation event, a first or second or third degree heart block event, and so forth. Predefined profiles such as disease profiles can be generated from offline training using labelled data, such as data associated with known diseases described above. The offline training can be based on, for example, labeled data from segmented denoised ECG signal data based on the R peaks at operation 606. The profile can also be associated with a status indicative of a health status or a fitness status of the individual, such as, for example, stress level or heart age. The status profile can include characteristic data that can be extracted from the training process, such as offline training 612. Alternatively, the status can also be determined by regression or by a classification model, using the processed ECG signal data.

Figure 8:
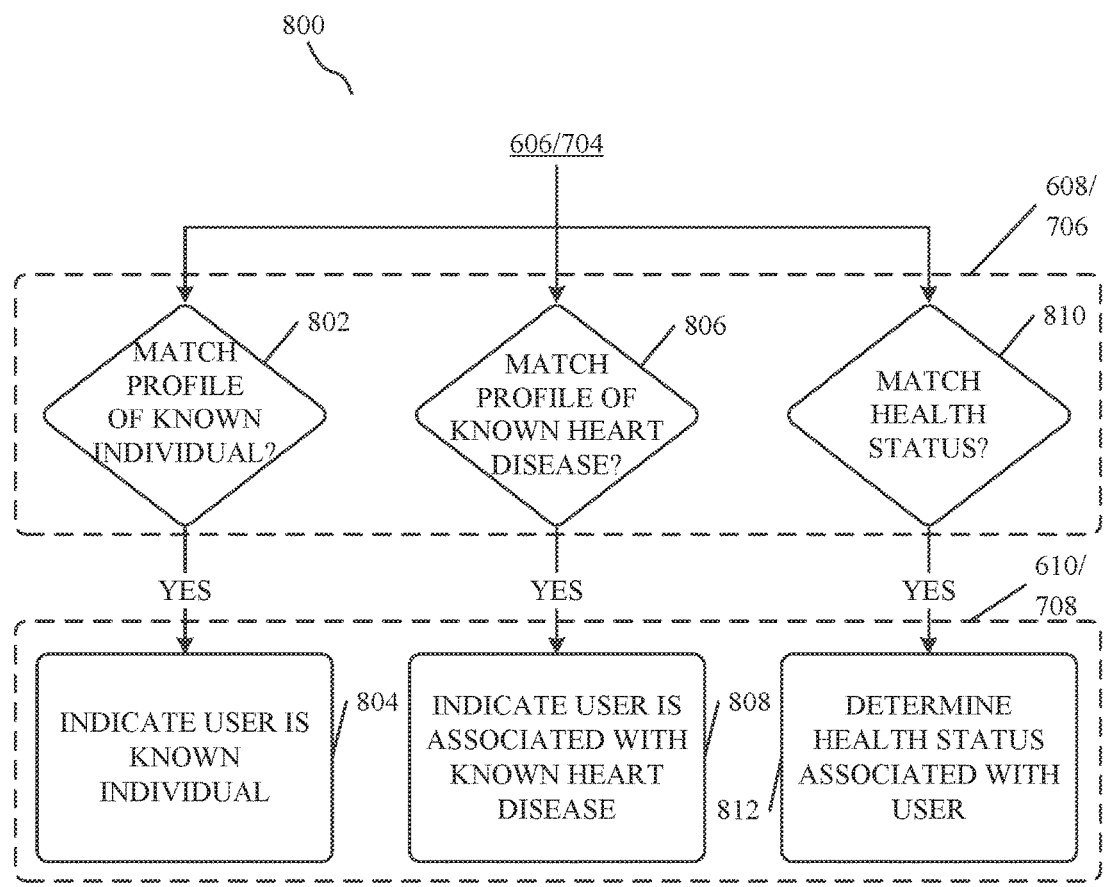
FIG. 8 is an example process of using multiple profiles to determine predicted labels according to implementations of this disclosure.

In some implementations, the template data or the characteristic data can be graphical data. In some other implementations, the template data and the characteristic data can include data indicative of graphical characteristics of the profile or the status. More than one predetermined profile or status can be used to find match. The processed ECG signal can be determined as matching to one of the one or more predetermined profiles. Several example profiles that can be used at operation 608 are shown in FIG. 8. As shown in FIG. 8, the profile can be, for example, a predefined profile of a known individual at 802, a predefined profile of a known heart disease at 806 or a profile associated with health status at 810.

Back to operation 608, in some implementations, the match can be determined based on similarity between the processed ECG signal and each profile. For example, for a profile, a quantity or value ("similarity score") can be calculated between the graphical characteristics (e.g., shape) of the processed ECG signal and the graphical characteristics of the template data. In this example, the highest similarity score can be used to indicate a match between the processed ECG signal and the profile or the status associated with the highest similarity score. In another example, for each profile or status, a similarity score can also be similarly calculated, and when the similarity score exceeds a predetermined threshold, it can be indicate a match between the processed ECG signal and the current profile or status under consideration. In still another example, the characteristic data of the processed ECG signal can be compared with the characteristic data of a status. Besides the above examples, various criteria can be used to determine the match between the processed ECG signal and the profiles. In addition, criteria based on other factors (e.g., trend, curve or cue) can also be used to determine the match between the processed ECG signal and the profiles.

If a match is found between the processed ECG and a profile or a status, process 600 proceeds to operation 610. Otherwise, process 600 goes back to operation 602, using a new ECG signal as input. At operation 610, a predicted label, e.g., a predicted event, associated with the individual is determined. The predicted label can include any data that is indicative of the matched profile or status at operation 608. Several examples of predicted labels are described in FIG. 8. For example, it can be indicated that the individual is the known individual when there is a match at operation 804 ("biometric identification"). It can be indicated that the individual is associated with a known heart disease at operation 808 ("disease identification"), or that a certain health status is associated with the individual at operation 812 ("status indicator").

After operation 610 is completed, process 600 can go back to operation 602, using a new ECG signal as input. Process 600 can be repeated continuously or periodically, until the wearable device exits the continuous mode, such as by being removed from the chest position or by being manually set by the individual.

Figure 7:
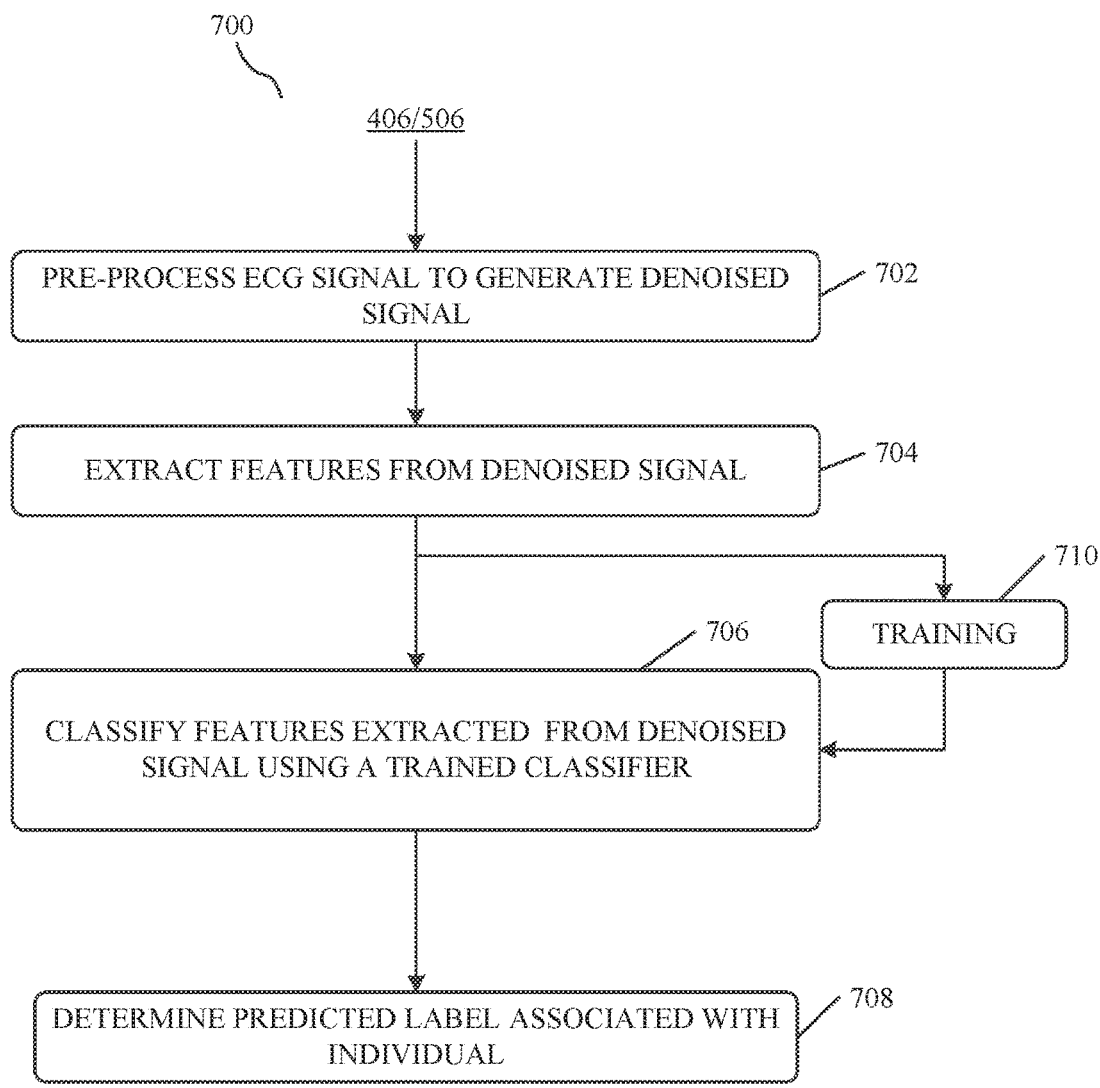
FIG. 7 is a flow diagram showing an example process for episodical ECG monitoring according to implementations of this disclosure.

FIG. 7 is a flow diagram showing an example process 700 for episodical monitoring of heart activity ("episodical mode"). Process 700 can be carried out following process 400 or 500, for example, upon determining that episodical mode is to be used for monitoring the ECG signals at operation 406 or 506. For example, process 700 can be triggered when it is determined that episodical mode is to be used for operating the wearable device at operation 506. Process 700 can also be activated by the individual by manually setting the operating mode as the episodical mode by software or hardware, such as by application program 310. The episodical mode can monitor heart activity of the individual on-demand, allowing more complex processing and analysis on the signals, and further provide feedback data to the individual. The feedback data can include data indicative of, for example, a heart disease or a health status. Where operations are substantially similar to those in process 600, reference will be made to the description above. There are some differences, however, that are pointed out in the following description of process 700.

At operation 702, similar to operation 602, the received ECG signals are pre-processed to generate a denoised signal. Sources of noise of the ECG signal can include, for example, EMG background, baseline wandering, powerline interference, and motion artifacts. The pre-processing can perform operations to reduce or remove the noise from the ECG signal.

At operation 704, one or more features are extracted from the denoised signal. The extracted features can include, for example, time domain features and frequency domain feature. The time domain features are features in a time domain representation of the signal, such as fiducial points of a graphical ECG signal, RR intervals, or wave fragments. The frequency domain features are features in a frequency domain representation of the signal, such as parameters and outputs from a Fast Fourier Transform (FFT), a wavelet transform, or the combination of an autocorrelation and a discrete cosine transform (AC-DCT).

At operation 706, the one or more features extracted from the denoised signal are classified using a trained classifier. The trained classifier can be one or more previously trained models that can be used for classification ("classification model"), e.g., a statistical model. The classifier can be trained using, for example, a learning technique such as various machine learning techniques. The classifier can be trained by, for example, offline or online training using labelled data, such as data with known diseases described above in process 600. For example, the predicted label can be determined using the classifier.

In a setup process, such as prior to its use for prediction or testing, the classifier can be trained at operation 710. The classifier can also be updated during the prediction process or testing by updating the parameters in the classification model. Labelled data associated with a known disease, a known individual, or a known health status can be used for training the classifier at 710. For example, the labelled data associated with a known disease can include, for example, data indicative of a premature ventricular contraction (PVC) event, data indicative of a premature atrial contraction (PAC) event, data indicative of a ventricular tachycardia event, an atrial fibrillation event, first, second or third degree heart block event, and so forth. The training can be based on, for example, labeled data from features extracted at operation 706. Data with different labels can be used to train the classifier to predict different labels, e.g., different disease labels or fitness statuses. Machine learning based techniques can be used for training at 710, which can include, for example, a support vector machine (SVM) technique, metric learning, deep learning etc. For example, the techniques can result in a weight that reflects the relative importance of an extracted feature as compared to all features, which can be used for determination at operation 706 or 708. In addition, operation 710 may be performed by a cloud server or elsewhere and may include data for extracted features collected from a relatively large population of individuals as training data.

At operation 708, one or more predicted labels associated with the individual are determined. The predicted labels can be determined by the classifier described at operation 706. The predicted label can be used, for example, to identify a predicted event (e.g., identification of a disease, a person or a fitness status), which can be indicated to the individual on a display of the wearable device or the computing device. The predicted label can be generated by the classifier based on the extracted one or more features. In some implementations, some or all of the features extracted at operation 706 can be provided to operation 710 to combine with other data for offline training.

After operation 708 is completed, process 700 can go back to operation 702, waiting for a new ECG signal as input. The new ECG signal can be generated, for example, when the individual performs an action by using a hand to touch the second electrode (on exterior surface) of the wearable device worn on the other hand again. Process 700 can be repeated once the new ECG signal is received, until the wearable device exits the episodical mode, such as by being removed from the wrist position or by being manually set by the individual FIG. 8 is an example process of using multiple profiles to determine predicted labels according to implementations of this disclosure. Process 800 can be carried out following operation 606 or operation 704, for example.

At operation 802, it is determined whether the processed ECG signal matches a predefined profile of a known individual. If it does, a first predicted label indicating the individual is the known individual is determined at operation 804. Operations 802-804 can be used, for example, for biometric identification.

At operation 806, it is determined whether the processed ECG signal matches a predefined profile of a known heart disease. If it does, a second predicted label indicating the individual is associated with the known heart disease is determined at operation 808. Operations 806-808 can be used, for example, for real-time heart disease monitoring. For example, the second predicted label can include an indicator for a heart disease event. The heart disease event can include, for example, a premature ventricular contraction (PVC) event, a premature atrial contraction (PAC) event, a ventricular tachycardia event, an atrial fibrillation event, a first or second or third degree heart block event, and so forth.

At operation 810, it is determined whether the processed ECG signal matches a health or fitness status. If it does, the health or fitness status is determined as associated with the individual at operation 812. The health or fitness status can relate to one or more of weight, heart rate, fatigue level, stress level, heart age, heart rate variability (HRV), and a heart condition. For example, the health status can be numerical or non-numerical data indicative of a stress level or fatigue level of the individual. For another example, the health status can be a numerical heart age or cardiac age of the individual.

The representation of predicted labels, such as the disease or biometric identification, the health or fitness status, which is often used as feedback to the individual can be, for example, a number, a text, a color, a sound, an icon, a vibration, or any combination of any visual, acoustic, and tactile output.

In some implementations, such as when a classifier is used to predict multiple labels, operations 802, 806, and 810 can be combined into a single classification operation, e.g., operation 706. Multiple labels generated at operation 706 can then be used to provide feedback data to the individual at, for example, operations 804, 808, and 812.

In some implementations, operations 602-610, 704-706, 802-812 and can be performed by an analysis component, either included in the wearable device (e.g., a smart watch) or another computing device (e.g., a smart phone or a server computer). When the analysis component is not included in the wearable device, the measurement component can communicate data with the analysis component via communication component 208 of the wearable device. For example, the communication can be established via a wireless connection (e.g., Bluetooth, infrared, Wi-Fi, NFC, ultrasound) or a wired connection (e.g., USB, audio jack).

The measurement component and the analysis component that perform the various operations described herein can be a same component, different components at a same device or at different devices. The wearable device and the computing device that performs the various operations described herein can be a same device or different devices. In some implementations, the measurement component and the accessory component can be a same component or different components.

The aspects herein can be described in terms of functional block components and various processing operations. Such functional blocks can be realized by any number of hardware and/or software components that perform the specified functions. For example, the described aspects can employ various integrated circuit components, e.g., memory elements, processing elements, logic elements, look-up tables, and the like, which can carry out a variety of functions under the control of one or more microprocessors or other control devices. Similarly, where the elements of the described aspects are implemented using software programming or software elements the disclosure can be implemented with any programming or scripting language such as C, C++, Java, assembler, or the like, with the various algorithms being implemented with any combination of data structures, objects, processes, routines or other programming elements. Functional aspects can be implemented in algorithms that execute on one or more processors. Furthermore, the aspects of the disclosure could employ any number of conventional techniques for electronics configuration, signal processing and/or control, data processing and the like. The words "mechanism" and "element" are used broadly and are not limited to mechanical or physical embodiments or aspects, but can include software routines in conjunction with processors, etc.

Implementations or portions of implementations of the above disclosure can take the form of a computer program product accessible from, for example, a computer-usable or computer-readable medium. A computer-usable or computer-readable medium can be any device that can, for example, tangibly contain, store, communicate, or transport a program or data structure for use by or in connection with any processor. The medium can be, for example, an electronic, magnetic, optical, electromagnetic, or a semiconductor device. Other suitable mediums are also available. Such computer-usable or computer-readable media can be referred to as non-transitory memory or media, and can include RAM or other volatile memory or storage devices that can change over time. A memory of an apparatus described herein, unless otherwise specified, does not have to be physically contained by the apparatus, but is one that can be accessed remotely by the apparatus, and does not have to be contiguous with other memory that might be physically contained by the apparatus.

Any of the individual or combined functions described herein as being performed as examples of the disclosure can be implemented using machine readable instructions in the form of code for operation of any or any combination of the aforementioned computational hardware. Computational code can be implemented in the form of one or more modules by which individual or combined functions can be performed as a computational tool, the input and output data of each module being passed to/from one or more further module during operation of the methods and systems described herein.

Information, data, and signals can be represented using a variety of different technologies and techniques. For example, any data, instructions, commands, information, signals, bits, symbols, and chips referenced herein can be represented by voltages, currents, electromagnetic waves, magnetic fields or particles, optical fields or particles, other items, or a combination of the foregoing.

While the disclosure has been described in connection with certain embodiments and implementations, it is to be understood that the invention is not to be limited to the disclosed embodiments but, on the contrary, is intended to cover various modifications and equivalent arrangements included within the scope of the appended claims, which scope is to be accorded the broadest interpretation so as to encompass all such modifications and equivalent structures as is permitted under the law.

All references, including publications, patent applications, and patents, cited herein are hereby incorporated by reference to the same extent as if each reference were individually and specifically indicated as incorporated by reference and were set forth in its entirety herein.

What is claimed is:

1. A method for monitoring heart activity using a wearable device, comprising:
   receiving, from the wearable device, an electrocardiograph (ECG) signal and a motion signal associated with an individual upon contact with the wearable device;
   in response to receiving the ECG signal and the motion signal associated with the individual, analyzing, by a computing device, a motion characteristic of the motion signal;
   determining, by the computing device, a position of the wearable device in contact with the individual based on the motion characteristic and data associated with a known body position stored in a memory, wherein the position of the wearable device in contact with the individual is determined based on the motion signal and the ECG signal;
   automatically selecting, by the computing device, a heart activity monitoring mode for operating the wearable device, based on the position of the wearable device in contact with the individual.

2. The method of claim 1, further comprising:
   in response to detecting the individual in contact with the wearable device for monitoring heart activity, generating, by the wearable device, the ECG signal and the motion signal associated with the individual, wherein the motion signal is at least one of an accelerometer signal and a gyroscope signal.

3. The method of claim 1, wherein the wearable device and the computing device are the same device.

4. The method of claim 1, further comprising:
   in response to determining the position of the wearable device in contact with the individual as a chest position, automatically selecting, by the computing device, the heart activity monitoring mode as a first mode, wherein monitoring of ECG signals received by the wearable device is continuous until the wearable device exits the first mode; and in response to determining the position of the wearable device in contact with the individual as a wrist position, automatically selecting, by the computing device, the heart activity monitoring mode as a second mode, wherein the monitoring of the ECG signals received by the wearable device is triggered and performed for an episodic period of time.

5. The method of claim 4, further comprising:
pre-processing the ECG signal to generate a denoised signal;
based on a determination of the wearable device being in the first mode, detecting R peaks from the denoised signal;
processing the ECG signal by segmenting the denoised signal based on the detected R peaks; and at least one of:
responsive to the processed ECG signal matching a predefined profile of a known individual, determining a first predicted label indicating the individual is the known individual;
responsive to the processed ECG signal matching a profile of a known heart disease, determining a second predicted label indicating that the individual is associated with the known heart disease; and
determining a health status for association with a profile of the individual based on the processed ECG signal, wherein the health status is related to one or more of weight, heart activity, fatigue level, stress level, heart age, heart activity variability, and heart condition associated with the individual.

6. The method of claim 4, further comprising:
pre-processing the ECG signal to generate a denoised signal;
based on a determination of the wearable device being in the second mode, extracting one or more features from the denoised signal;
classifying the one or more features extracted from the denoised signal using a trained classifier to determine at least one of:
a first predicted label indicating the individual is the known individual;
a second predicted label indicating that the individual is associated with the known heart disease; and
a health status for association with a profile of the individual based on the processed ECG signal, wherein the health status is related to one or more of weight, heart activity, fatigue level, stress level, heart age, heart activity variability, and heart condition associated with the individual.

7. The method of claim 1, wherein the position of the wearable device in contact with the individual is selected from at least a wrist position and a chest position, and the heart activity monitoring mode for operating the wearable device is selected from at least a first mode indicative of continuous monitoring of ECG signals for a chest position and a second mode indicative of episodic monitoring of the ECG signals for a wrist position, wherein the ECG signals are received by the wearable device.

8. The method of claim 7, further comprising:
in response to the position of the wearable device in contact with the individual being determined to be in the chest position, identifying a unipolar chest lead for measuring the ECG signals, wherein the unipolar chest lead comprises one of leads V1, V2, V3, V4, V5, and V6; and
in response to the position of the wearable device in contact with the individual being determined to be in the wrist position, identifying a bipolar limb lead formed upon the individual's contact with a first and second electrodes of the wearable device, wherein the bipolar limb lead comprises one of leads I, II, and III.

9. The method of claim 1, wherein the wearable device comprises a measurement component configured to be removably attached to at least one of a first accessory component capable of being attached to the individual's chest and a second accessory component capable of being worn on the individual's wrist.

10. A system, comprising:
a measurement component, comprising:
an electrocardiogram (ECG) sensor, comprising:
a first electrode, wherein a first ECG lead configured to generate an ECG signal is formed upon an individual's contact with the first electrode; and
a second electrode, wherein a second ECG lead configured to generate the ECG signal is formed upon the individual's contact with the first and second electrodes; and
a motion sensor configured to generate a motion signal based on the individual's movement; and
an analysis component, comprising:
a non-transitory memory; and
a processor configured to execute instructions stored in the non-transitory memory to:
receive, from the ECG sensor, the ECG signal;
receive, from the motion sensor, the motion signal;
analyze a motion characteristic of the motion signal;
determine a position of the measurement component in contact with the individual based on the motion characteristic and data associated with a known body position stored in the non-transitory memory, wherein the position of the measurement component in contact with the individual is determined based on the motion signal and the ECG signal; and
automatically select, without user input, a heart activity monitoring mode for operating the measurement component, based on the position of the measurement component in contact with the individual.

11. The system of claim 10, wherein the processor is further configured to execute instructions stored in the non-transitory memory to: determine the position of the measurement component in contact with the individual based on at least one of the motion signal and the ECG signal.

12. The system of claim 10, wherein the processor is further configured to execute instructions stored in the non-transitory memory to:
in response to a determination that the position of the measurement component in contact with the individual is a chest position, automatically select, without user input, the heart activity monitoring mode for operating the measurement component as a first mode, wherein monitoring of ECG signals received by the measurement component is continuous until the wearable device exits the first mode; and
in response to a determination that the position of the measurement component in contact with the individual is a wrist position, automatically select, without user input, the heart activity monitoring mode for operating the measurement component as a second mode, wherein the monitoring of the ECG signals received by the measurement component is triggered and performed for an episodic period of time.

13. The system of claim 12, wherein the processor is further configured to execute instructions stored in the non-transitory memory to:
   pre-process the ECG signal to generate a denoised signal;
   based on a determination of the measurement component being in the first mode, detect R peaks from the denoised signal;
   process the ECG signal by segmenting the denoised signal based on the detected R peaks;
   responsive to the processed ECG signal matching a predefined profile of a known individual, determine a first predicted label indicating the individual is the known individual; and
   responsive to the processed ECG signal matching a profile of a known heart disease, determine a second predicted label indicating that the individual is associated with the known heart disease.

14. The system of claim 12, wherein the processor is further configured to execute instructions stored in the non-transitory memory to:
   pre-process the ECG signal to generate a denoised signal;
   based on a determination of the measurement component being in the second mode, extract one or more features from the denoised signal;
   classify the one or more features extracted from the denoised signal using a trained classifier to determine:
      a predicted label indicating the individual is a known individual; and
      a health status associated with the known individual based on the processed ECG signal, wherein the health status comprises a heart age.

15. The system of claim 12, wherein the processor is further configured to execute instructions stored in the non-transitory memory to:
   in response to the position of the measurement component in contact with the individual being determined to be in the chest position, identify a unipolar chest lead for measuring the ECG signals, wherein the unipolar chest lead comprises one of leads V1, V2, V3, V4, V5, and V6; and
   in response to the position of the measurement component in contact with the individual being determined to be in the wrist position, identify a bipolar limb lead formed upon the individual's contact with a first and second electrodes of the measurement component, wherein the bipolar limb lead comprises one of leads I, II, and III.

16. The system of claim 12, wherein the measurement component is configured to be removably attached to at least one of a first accessory component capable of being attached to the individual's chest and a second accessory component capable of being worn on the individual's wrist.

17. The system of claim 10, wherein the ECG signal and the motion signal associated with the individual are generated by the measurement component upon detecting the individual in contact with the measurement component for monitoring heart activity, and the motion sensor comprises at least one of an accelerometer and a gyroscope.

18. An apparatus for monitoring heart activity, comprising:
   a non-transitory memory; and
   a processor configured to execute instructions stored in the non-transitory memory to:
      receive an electrocardiograph (ECG) signal and a motion signal associated with an individual upon contact with a wearable device;
      in response to receiving the ECG signal and the motion signal associated with the individual, analyze a motion characteristic of the motion signal;
      determine a contact position of the wearable device based on the motion characteristic and data associated with a known body position stored in the non-transitory memory, wherein an electrode of the wearable device attaches to a skin of the individual, wherein the contact position of the wearable device is determined based on the motion signal and the ECG signal; and
      automatically select a heart activity monitoring mode for operating the wearable device, based on the contact position of the wearable device, wherein the contact position of the wearable device is selected from at least a wrist position and a chest position, and the heart activity monitoring mode for operating the wearable device is selected from at least a first mode indicative of continuous monitoring of ECG signals and a second mode indicative of episodic monitoring of the ECG signals.

19. The apparatus of claim 18, wherein the instructions stored in the non-transitory memory executed by the processor further comprise instructions to:
   pre-process the ECG signal to generate a denoised signal;
   based on a determination of the measurement component being in the first mode indicative of continuous monitoring of ECG signals,
   detect R peaks from the denoised signal;
   process the ECG signal by segmenting the denoised signal based on the detected R peaks
   in response to the processed ECG signal matching a profile of a known heart disease, determine a predicted label indicating that the individual is associated with the known heart disease; and
   based on a determination of the measurement component being in the second mode indicative of episodic monitoring of ECG signals,
   extract one or more features from the denoised signal;
   classify the one or more features extracted from the denoised signal using a trained classifier to determine:
      a predicted label indicating the individual is the known individual; and
      a health status for association with a profile of the individual based on the processed ECG signal, wherein the health status is related to one or more of weight, heart activity, fatigue level, stress level, heart age, heart activity variability, and heart condition associated with the individual.

* * * * *